United States Patent [19]

Kuypers

[11] Patent Number: 4,492,622
[45] Date of Patent: Jan. 8, 1985

[54] CLARK CELL WITH HYDROPHYLIC POLYMER LAYER

[75] Inventor: Martinus H. Kuypers, Veldhoven, Netherlands

[73] Assignee: Honeywell Inc., Minneapolis, Minn.

[21] Appl. No.: 529,183

[22] Filed: Sep. 2, 1983

[30] Foreign Application Priority Data

Sep. 3, 1982 [EP] European Patent Office ...... 82108135.3

[51] Int. Cl.³ .................... G01N 27/30; G01N 27/40
[52] U.S. Cl. ................................ 204/403; 128/635; 204/415
[58] Field of Search ............ 204/415, 1 P, 403, 416; 128/635; 29/592 R

[56] References Cited

U.S. PATENT DOCUMENTS 2,913,386 11/1959 Clark ............................. 204/415

Primary Examiner—G. L. Kaplan
Attorney, Agent, or Firm—Mitchell J. Halista; Trevor B. Joike

[57] ABSTRACT

An electro-chemical cell for determining a particular property or component of a fluid includes a cathode electrode, an anode electrode spaced from the cathode, an electrolyte filling a space containing the cathode and anode electrodes, a selectively permeable membrane separating the electrodes and the electrolyte from the fluid to be analyzed and a layer of a hydrophylic polymer provided between a membrane and the electrodes and covering at least the cathode wherein the membrane has at least one hole in it for allowing electrolytic component of the fluid to enter the hydrophylic polymer layer and that the distance between the holes and the membrane and the cathode is relatively large as compared to the width of the cathode.

9 Claims, 3 Drawing Figures 4,492,622

CLARK CELL WITH HYDROPHYLIC POLYMER LAYER

BACKGROUND OF THE INVENTION

1. Field of the Invention

This invention relates to electro-chemical cells. More specifically, the present invention is directed to an electro-chemical cell utilizing a membrane for separating the cell components from a medium being tested.

2. Description of the Prior Art

Cells of this type are for instance used for determining the oxygen or carbon dioxide content of a fluid such as blood or its pH value. One well-known cell of this kind is the so-called Clark Cell used for measurements in biological media which cell includes a selectively permeable membrane for separating the cell components from the media. For this purpose reduction of the dimensions of such cells is desirable, in particular for measuring inside blood vessels. Since the metal of the anode as well as the electrolyte are consumed by the electro-chemical process during oxygen detection, a reasonable amount of both materials must be available in the cell. This is one of the limits for reducing the size of a Clark Cell. The required amount of electrolyte depends on the desired sensitivity of the sensor. This in turn is a function of the dimensions of the cathode and the thickness and permeability of the membrane. In most cases a small diameter of the cathode is favorable for obtaining a high-quality measuring signal in order to keep this signal unaffected by the flow conditions of the biological medium. If the resulting electrical signal, however, is too small, interference and noise signals will disturb the reliability of the measuring signal. The use of small cathodes formed as a circle, spiral or line results in a high electrical current. A high current consumes a relatively large amount of electrolyte which has to be stored in the cell. The combination of an optimum shape and extension of the cathode and the required miniaturization of the sensor, therefore, require a compromise.

The electrolyte which is necessary for the electro-chemical process in a Clark Cell is in a sufficient amount available in the biological medium. In the conventional Clark Cell one of the functions of the membrane is to define the oxygen flux to the cathode. The other function of the membrane is to separate the electrolyte in the Clark Cell from the electrolyte in the biological medium in order to avoid mixing of the two electrolytes. A direct contact between the biological medium and the cathode of the Clark Cell further would reduce the functionality of the cell because of adhesion of proteins to the surface of the cathode which would reduce the effective surface area of the cathode.

A second type of the Clark Cell is known using a porous membrane made of methycellulose, polystyrene or a hydrophylic polymer such as HEMA (hydroxyethylmetacrylate), which is simultaneously used for defining the oxygen flux on the one side and to allow the transport of the electrolyte from the biological medium into the Clark Cell. One advantage of this type of cell is the possibility to store the dry sensor over a long period. The electrolyte enters the cell as soon as it is poured into contact with the biological medium. A disadvantage of this cell, however, is that the membrane may be deformed or swell in an undefined manner which alters the oxygen flux and therewith the sensitivity of the cell. This type of a Clark Cell, therefore, has to be recalibrated relatively often.

In a third type of Clark Cell the necessary amount of electrolyte is stored as dry salt under the membrane so that this cell can be stored in dry form over a long period of time. Activation of the cell is accomplished as soon as water vapor migrates through the membrane and dissolves the salt, therewith forming the liquid electrolyte. However, for this type of Clark Cell a long activation period of about four hours is required before the cell becomes fully operable.

SUMMARY OF THE INVENTION

It is the object of the invention to provide a new electro-chemical cell of the type as defined above in which the electrolyte is supplied by the fluid under measurement without the danger that deformations of the membrane change the sensitivity of the cell in a non-controlled manner. The new cell should be capable of being miniaturized and should be suitable for medical and biological application, i.e. sterilization should be no problem. These objects and further improvements are accomplished by an electro-chemical cell comprising a cathode electrode and spaced therefrom an anode electrode, whereat a space engaging the electrodes is adapted to be filled with an electrolyte, a selectively permeable membrane separating the electrodes and the space from a fluid to be analyzed and a thin layer of hydrophylic polymer between the membrane and the electrodes covering at least the cathode and having at least one hole in the membrane for allowing an electrolytic component of the fluid to enter the hydrophylic polymer layer with a distance between the hole and the cathode larger than the width of the cathode.

BRIEF DESCRIPTION OF THE DRAWINGS

A better understanding of the present invention may be had when the following detailed description is read in connection with the accompanying drawings, in which FIG. 3 shows a partial cross-section of another modification of the cell structure shown in Fig 1.

DESCRIPTION OF THE PREFERRED EMBODIMENT

Figure 1:
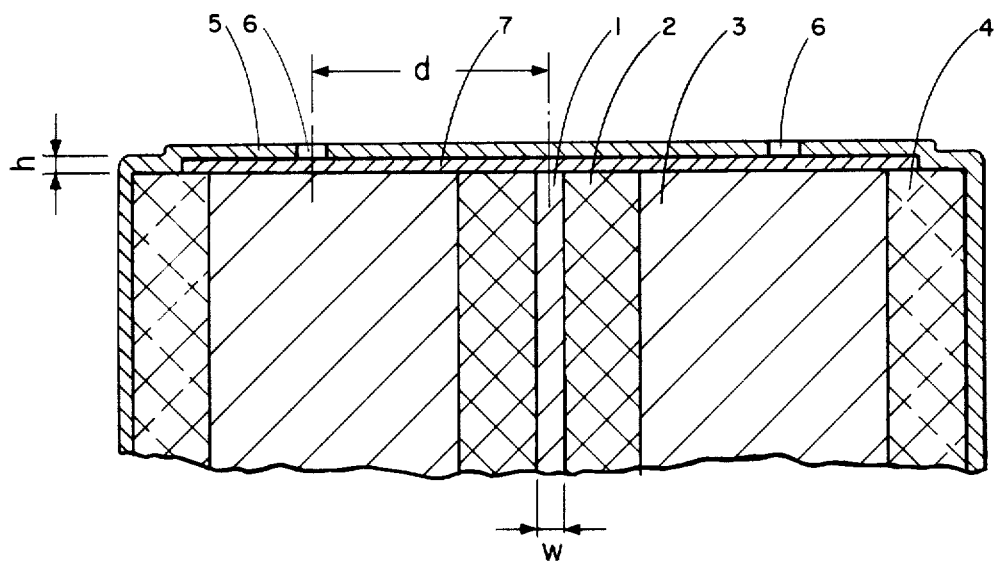
FIG. 1 shows a cross-section of an electro-chemical cell embodying and example of the present invention.

The present invention is characterized by the provision of a known porous hydrophobic membrane having holes at defined locations allows passage of the electrolyte into and through the hydrophylic polymer only at those locations from where the electrolyte moves into the space between the electrodes. The hydrophylic polymer is sufficiently permeable for the electrolyte in the biological medium, but its pores are small enough not to allow biological molecules such as proteins to pass. A well-known hydrophobic membrane may be formed by the application of bis-azide sensitizers to cyclized-rubber as discussed on page 40 of the publication "Photoresist Materials and Processes" by W. S. DeForest published by McGraw-Hill in 1978. The hydrophylic polymer, therefore, is almost impermeable for proteins. There is no danger of poisoning the cathode. On the other side it is important that the oxygen diffusion through the holes in the membrane and via the capillaries in the hydrophylic polymer to the cathode is essentially smaller than the oxygen diffussion through the membrane. This is accomplished by locating the holes far enough from the cathode, with other words the distance between the holes and the cathode is relatively large as compared to the width of the cathode. The cathode can be made circular, spiral or line-shaped and could have a width of $5\mu$ and a length of $1000\mu$. This cell can be stored sterile and dry over a long period of time.

The hydration and polarization of the cell is accomplished rather quickly. Within a few minutes after inserting the sensor into a calibration liquid or into the bloodstream the sensor is operable and gives a stable signal. The lifetime of the sensor is determined by the amount of anode material, for instance silver. For measuring the arterial oxygen content it may be supplied with a sufficient amount for reaching a lifetime of several days. The silver anode may be covered by the hydrophylic polymer layer or it can be located externally on the system, consisting of the cathode, the hydrophylic polymer layer and the membrane.

A further advantage of the hydrophylic polymer layer is that it can be used for immobilizing biochemically active elements. In known Clark Cells for sensing glucose the glucoseoxidase enzyme is used. This enzyme can only be reached by molecules which penetrate the hydrophylic polymer so that proteins do not reach the enzyme if it is situated close to the electrodes.

The new electro-chemical cell can also be used as an ion-selective sensor for measuring the pH value of a medium. In this case an ion-selective membrane is covered by the hydrophylic polymer and a hydrophobic membrane provided with holes so that the ion-selective membrane is sufficiently protected against the blood and in fact, is only in contact with the water-phase of the blood and smaller biochemical molecules.

Further preferred modifications and improvements of the invention are described in the subclaims. The invention will be described with respect to two embodiments schematically shown in the drawings.

FIG. 1 shows only those portions of a Clark Cell which are of interest in connection with the present invention. Further details can be taken from U.S. Pat. No. 2,913,356. A cathode wire 1 is surrounded by an insulating rod 2, which in turn is surrounded by a hollow cylinder 3 forming the anode. A further hollow cylinder 4 of insulating material protects the anode. The entire system is covered by a selectively permeable hydrophobic membrane 5 which is provided with several through-holes 6. Located between the front surfaces of the cathode 1 and the anode 3 on the one side and the membrane 5 on the other side is a layer 7 of hydrophylic polymer which in the shown embodiment covers the front surfaces of both electrodes 1 and 3. For activating the cell, electrolyte has to be brought into contact with cathode 1 and the anode 3. Instead of a wire a cylinder or other cathode structure of small diameter and large length may be used.

When using the cell, the front surface of membrane 5 is exposed to the biological medium so that the electrolyte component of the medium can pass through the holes 6 and through the hydrophylic polymer layer 7 into contact with the electrodes. In this way the cell is activated. It must be prevented, however, that the direct access of oxygen through the holes 6 results in a change or increase of the oxygen diffusion through the selectively permeable membrane 5 to the electrodes. For this reason the distance (d) of hole 6 from the cathode 1 is by far larger, for instance five times larger than the width (w) of the active front surface area of cathode 1. The thickness (h) of the hydrophylic polymer layer 7 is very small, preferably less than $4\mu$. Most or essentially all of the oxygen reaching cathode 1, therefore, stems from diffusion through membrane 5 and the oxygen portion entering through hole 6 and traveling along hydrophylic polymer layer 7 can be neglected. This layer may be made of a hydrogel such as polyvinyl alcohol, polyvinyl pyrrolidone, polyacrylamide, hydroxyethylmetacrylate or derivatives of these compounds. The diameter of the hole 6 is small compared with distance d. The cathode preferably is made of noble metal such as gold and the anode may consist of silver. The hydrophylic polymer acts as a sieve which is permeable for the electrolyte, oxygen, carbon dioxide and relatively small biological organic molecules such as glucose, but it is impermeable for large biological molecules such as proteins.

Figure 2:
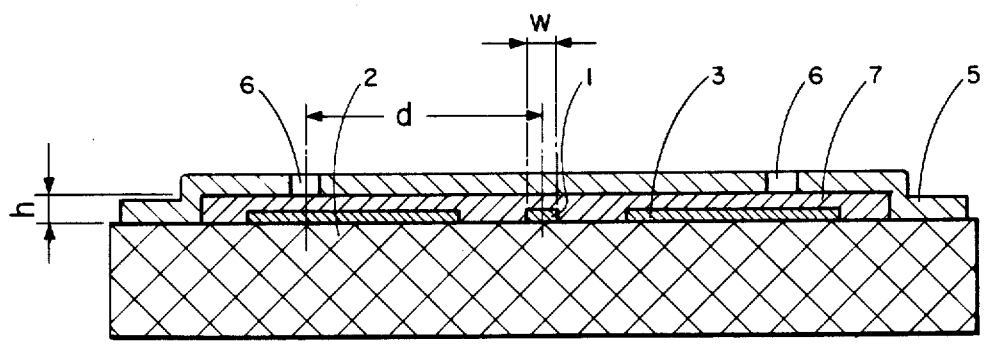
FIG. 2 shows a cross-section of a modification of the cell structure shown in FIG. 1

In the second embodiment shown in FIG. 2 a silicon substrate 2 supports cathode 1 and anode 3 which are deposited on the substrate 2 in the known manner of forming printed or integrated circuits. Both electrodes again are covered by a layer 7 of hydrophylic polymer which is protected on the outside by means of a membrane 5. Hole 6 within the said membrane permits access of the electrolyte to the hydrophylic polymer layer so that the electrolyte can pass along this layer to cathode 1 for activating the cell. Oxygen or any other constituent of the fluid under examination diffuses through membrane 5 and layer 7 to cathode 1, therewith influencing the electro-chemical process between electrodes 1 and 3.

In FIG. 3, there is shown a partial cross-section of another modification of the cell structure shown in FIG. 1. In this modification, an ion-selective membrane 8 is arranged to separate the electrodes 1 and 3 from the hydrophylic layer 7 and the hydrophobic membrane 5 provided with the holes 6. In this arrangement the cell can be used as an ion-selective sensor for measuring the pH of a medium while the ion-selective membrane 8 is protected and is only in contact with the water-phase and smaller biochemical molecules of the medium. The electrodes 1 and 3 are connected to a source of DC and the amount of current induced by the reduction and oxidation process at the cathode and the anode, respectively, is a measure for determining the content of oxygen within the biological medium into which the sensor is inserted. Instead of silicon another insulating substrate such as glass or ceramics may be used. Silicon is preferred if the cell is produced by the processes of manufacturing integrated circuits. If thin film or thick film technology is used for making the cell, the substrate may consist of glass or ceramics.

I claim:

1. Electro-chemical cell for determining a particular property or component of a fluid comprising a cathode electrode (1) and spaced therefrom an anode electrode (3), whereat a space engaging said electrodes is adapted for being filled with an electrolyte, and comprising a selectively permeable membrane (5) separating said electrodes and said space from the fluid characterized in that a thin layer (7) of hydrophylic polymer is provided between said membrane (5) and said electrodes (3, 4) covering at least the cathode (4);

that the membrane (5) has at least one hole (6) in it for allowing an electrolytic component of the fluid to enter said hydrophylic polymer layer (7); and that the distance (d) between the hole(s) (6) and the cathode (1) is larger than the width (w) of the cathode (1).

2. A cell according to claim 1, characterized in that both the cathode (1) and the anode (3) are covered with a layer (7) of hydrophylic polymer.

3. A cell according to claim 1, characterized in that the hydrophylic polymer layer (7) comprises a hydrogel taken from the group consisting of polyvinyl alcohol, polyvinyl pyrrolidone, polyacrylamide, hydroxyethylmetacrylate and derivatives of these compounds.

4. A cell according to claim 1, characterized in that the membrane (5) is made of hydrophobic polymer.

5. Cell according to claim 1, characterized in that it is an oxygen sensor.

6. A cell according to claim 1 characterized by an ion-selective membrane between said electrodes and said layer of hydrophylic polymer to form an ion-selective sensor.

7. A cell according to claim 1, characterized in that the hydrophylic polymer layer (7) is less than $4\mu$ thick.

8. A cell according to claim 1, characterized by an insulating substrate (2) supporting the electrodes (1,3) made of a material taken from the group consisting of silicon, glass and ceramics.

9. A cell as set forth in claim 1 wherein the distance between said holes and said cathode is at least five times larger than the width of said cathode.

* * * * *